United States Patent
Tierney et al.

(10) Patent No.: US 11,969,503 B2
(45) Date of Patent: *Apr. 30, 2024

(54) METHOTREXATE COMPOSITION

(71) Applicant: Rosemont Pharmaceuticals Ltd., Leeds (GB)

(72) Inventors: Carl Tierney, Leeds (GB); Stacey Powell, Leeds (GB); Peter Braybrooke, Leeds (GB); Geraint Jones, Leeds (GB)

(73) Assignee: Rosemont Pharmaceuticals Ltd, Leeds (GB)

( * ) Notice: Subject to any disclaimer, the term of this patent is extended or adjusted under 35 U.S.C. 154(b) by 161 days.

This patent is subject to a terminal disclaimer.

(21) Appl. No.: 17/470,131

(22) Filed: Sep. 9, 2021

(65) Prior Publication Data

US 2021/0401742 A1 Dec. 30, 2021

Related U.S. Application Data

(63) Continuation of application No. 16/839,178, filed on Apr. 3, 2020, now Pat. No. 11,116,724, which is a continuation of application No. 16/266,305, filed on Feb. 4, 2019, now Pat. No. 10,610,485, which is a continuation of application No. 15/821,242, filed on Nov. 22, 2017, now Pat. No. 10,231,927, which is a continuation of application No. 15/019,244, filed on Feb. 9, 2016, now Pat. No. 9,855,215, which is a continuation of application No. 13/733,031, filed on Jan. 2, 2013, now Pat. No. 9,259,427.

(30) Foreign Application Priority Data

Jan. 6, 2012 (GB) .................................... 1200192

(51) Int. Cl.
*A61K 9/08* (2006.01)
*A61K 9/00* (2006.01)
*A61K 31/519* (2006.01)
*A61K 47/02* (2006.01)
*A61K 47/12* (2006.01)
*A61K 47/14* (2017.01)

(52) U.S. Cl.
CPC ............ *A61K 9/08* (2013.01); *A61K 9/0053* (2013.01); *A61K 9/0095* (2013.01); *A61K 31/519* (2013.01); *A61K 47/02* (2013.01); *A61K 47/12* (2013.01); *A61K 47/14* (2013.01)

(58) Field of Classification Search
CPC ................................ A61K 31/519; A61K 9/08
See application file for complete search history.

(56) References Cited

U.S. PATENT DOCUMENTS

| | | | |
|---|---|---|---|
| 9,259,427 B2 | 2/2016 | Tierney et al. | |
| 9,855,215 B2 | 1/2018 | Tierney et al. | |
| 10,231,927 B2 | 3/2019 | Tierney et al. | |
| 10,610,485 B2 | 4/2020 | Tierney et al. | |
| 11,116,724 B2* | 9/2021 | Tierney | ............. A61P 19/02 |
| 2005/0101605 A1 | 5/2005 | Ahmed et al. | |
| 2010/0016326 A1 | 1/2010 | Will | |
| 2010/0239646 A1 | 9/2010 | Nair | |

FOREIGN PATENT DOCUMENTS

WO 2008009476 1/2008

OTHER PUBLICATIONS

Rote Liste Service GMBH Ed, Methotrexat-biosyn 2.5mg/Methotrexat-biosyn Liquid 25mg/50mg/500mg, Jan. 1, 1999, 1 Page.
Methotrexate Sodium Oral Solution Reference (www.fda.gov/ohrms/dockets/dailys/02/May02/051702/02p-0226-cp00001-04-Tab-03-vol1.pdf-henceforth MSOS) (accessed Apr. 8, 2014).
Pharmaguideline ("Preparation of Buffer Solutions", Sep. 2010, accessed from http://www.pharmaguideline.com/2010/09/preparation-of-butter-solutions.html on Apr. 8, 2014).
Stuar, J. F. B. et al., "Bioavalability of Methotrexate: Implications for Clinical Use", Cancer, Chemotherapy and Pharmacology, 3, 239-241 (1979).
Methotrexate 2.5-mg/5-mL Oral Liquid, Formulations, International Journal of Pharmaceutical Compounding, vol. 3, No. 6, Nov./Dec. 1999.

* cited by examiner

*Primary Examiner* — James D. Anderson
(74) *Attorney, Agent, or Firm* — GableGotwals

(57) ABSTRACT

A Methotrexate composition for oral administration is provided comprising a pharmaceutically acceptable salt of Methotrexate and an aqueous carrier agent. The Methotrexate salt is substantially or completely soluble in the aqueous carrier agent, forming an aqueous solution. There is also provided a method of manufacturing a Methotrexate composition for oral administration, comprising mixing a pharmaceutically acceptable salt of Methotrexate with an aqueous carrier agent until the Methotrexate salt is substantially or completely soluble in the carrier agent to form an aqueous solution.

20 Claims, 1 Drawing Sheet

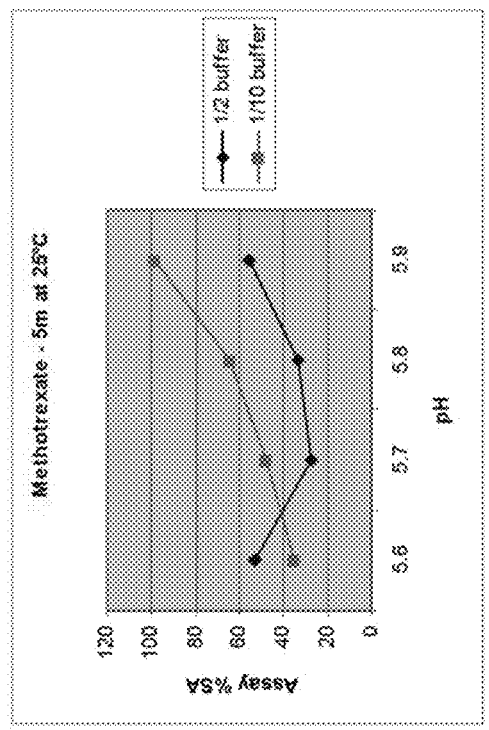

METHOTREXATE COMPOSITION

CROSS-REFERENCE TO RELATED APPLICATION

This application is a continuation application of U.S. Ser. No. 16/839,178 filed Apr. 3, 2020 which is a continuation application of U.S. Ser. No. 16/266,305 filed Feb. 4, 2019 (U.S. Pat. No. 10,610,485) which is a continuation application of U.S. Ser. No. 15/821,242 filed Nov. 22, 2017 (U.S. Pat. No. 10,231,927) which is a continuation of U.S. Ser. No. 15/019,244 filed Feb. 9, 2016 (U.S. Pat. No. 9,855,215) which is a continuation of U.S. Ser. No. 13/733,031 filed Jan. 2, 2013 (U.S. Pat. No. 9,259,427) which claims priority to British Patent Application No. 1200192.1 filed 6 Jan. 2012, each of which is incorporated herein by reference.

STATEMENT REGARDING FEDERALLY SPONSORED RESEARCH OR DEVELOPMENT

Non-applicable

THE NAMES OF THE PARTIES TO A JOINT RESEARCH AGREEMENT

Non-applicable

REFERENCE TO A "SEQUENCE LISTING"

Non-applicable

BACKGROUND OF THE INVENTION

This invention relates to a Methotrexate composition, a method of use thereof and a method of manufacture.

Methotrexate has the systemic name of (2S)-2-[(4-{[2,4-diaminopteridin-6-yl)methyl](methyl)amino}benzoyl) amino]pentanedioic acid or $C_{20}H_{22}N_8O_5$. It is used as a folic acid antagonist, in the treatment of neoplastic disease, such as trophoblastic neoplasms and leukaemia and in the control of severe recalcitrant psoriasis which is not responsive to other forms of therapy. It is also used to treat a wide range of tumours, such as acute leukemias, Non-Hodgkin's lymphoma, soft tissue and bone sarcomas, solid tumours like breast, lung, head, neck, bladder, cervical, ovarian and testicular cancer, as an immunosuppressant and as an anti-metabolite.

Use of Methotrexate containing compositions for oral administration in tablet form is known. However, a solid tablet form may be unsuitable for patients who have difficulty swallowing, such as children, elderly patients, stroke patients and/or the like. In order to overcome this problem, it would be beneficial to provide a Methotrexate containing composition as an oral solution which is palatable, as well as physically and chemically stable. However, Methotrexate has been found to precipitate out of solution over time.

BRIEF SUMMARY OF THE INVENTION

It is therefore an aim of the present invention to provide an optimised Methotrexate composition suitable for oral administration which overcomes the abovementioned problems.

It is a further aim of the present invention to provide a method of manufacturing an improved Methotrexate composition suitable for oral administration.

It is a yet further aim of the present invention to provide a method of use of an improved Methotrexate composition for oral administration.

According to a first aspect of the present invention there is provided a Methotrexate composition suitable for oral administration, said composition containing a pharmaceutically acceptable salt of Methotrexate and an aqueous carrier agent in which the Methotrexate salt is substantially or completely soluble to form an aqueous solution.

The Methotrexate solution as described herein is stable in that it remains substantially or wholly dissolved in the aqueous agent for a prolonged or predetermined period of time. The term "solution" is in contrast to a Methotrexate containing "suspension" wherein the Methotrexate salt is un-dissolved and homogenously dispersed in a suspension medium.

Any pharmaceutically acceptable soluble salt of Methotrexate can be used. Preferably the pharmaceutically acceptable soluble salt of Methotrexate used is Methotrexate disodium. This salt is preferably in a powder form prior to addition to the aqueous carrier agent.

Preferably the pH of the composition is within the pH range of 6-7. It has been found by the Applicants that at pH values below 6.0 the Methotrexate is seen to precipitate out of solution over time and the lower the pH1 the greater the amount of precipitate seen. At pH values above 7.0 there is an increase in degradation that will limit the shelf life of the composition.

Further preferably the pH of the composition is within the pH range of 6.1-6.5. Yet further preferably the pH of the composition is at pH 6.25+/−0.15.

Preferably the aqueous carrier agent is or includes water, purified water and/or the like.

Preferably the composition includes one or more buffer agents or pH modifying agents to adjust the pH to the preferred range. The combination of the pH range used and the buffer strength of the one or more buffer agents typically prevent precipitation of the Methotrexate and maintain the composition as a substantially clear solution.

The one or more buffer agents can include any or any combination of Citric Acid, Sodium Citrate, Sodium Dihydrogen Phosphate, Disodium Hydrogen Phosphate, Trometamol (Tris), Hydrochloric Acid, Ascorbic Acid, Sodium Ascorbate, any of the abovementioned sodium salts replaced with potassium salts and/or the like.

Preferably two or more buffer agents are provided to form a buffer system, such as a Citric Acid-Sodium Citrate Buffer, Sodium Dihydrogen Phosphate-Disodium Hydrogen Phosphate Buffer, Trometamol (Tris)-Hydrochloric Acid Buffer, Trometamol (Tris)-Citric Acid Buffer, Ascorbic Acid-Sodium Ascorbate Buffer, any of the abovementioned sodium salts replaced with potassium salts and/or the like.

In a preferred embodiment the two or more buffer agents include citric acid monohydrate and disodium hydrogen phosphate.

Preferably the resulting buffer strength used is in the range of 2 millimolar to 200 millimolar. Further preferably the resulting buffer strength used is in the range of 2-20 millimolar to maximise the stability of the Methotrexate and shelf life of the oral solution product.

Preferably the composition includes one or more preserving agents to increase the shelf life of the composition. The one or more preserving agents could include any or any combination of Sodium Methyl Hydroxybenzoate, Sodium Ethyl Hydroxybenzoate, Sodium Propyl Hydroxybenzoate, Sodium Benzoate, Potassium Sorbate and/or the like.

Preferably the composition includes one or more flavouring compounds and/or sweetening agents to mask the taste of the Methotrexate salt contained therein and/or to make the resulting composition more palatable. The one or more flavouring compounds and/or sweetening agents can include Sucralose, Acesulfame K, any other water soluble sweetener, Raspberry Flavour 545742E and/or the like that is/are compatible with the Methotrexate salt used in the composition.

In one embodiment the Methotrexate composition can be used in the treatment of or for the manufacture of a medicament for the treatment of any or any combination of a folic acid antagonist, an anti-neoplastic agent, an immunosuppressant, an anti-metabolite, neoplastic disease, malignant disease, psoriasis, Crohn's disease, rheumatoid arthritis, polyarthritic forms of active juvenile idiopathic arthritis, juvenile dermatomyositis, vasculitis, uvenlitis, systemic lupus erythematosus, localised scleroderma and sarcoidrosis.

Preferably the pharmaceutically acceptable dosage of the Methotrexate salt used in the composition is 2.5 mg/5 ml, 5 mg/5 ml, 10 mg/5 ml or in the range of 0.05 mg/1 ml to 20 mg/1 ml.

In a preferred embodiment the composition includes a pharmaceutically acceptable salt of Methotrexate, one or more buffering agents, one or more preserving agents, one or more sweetener agents and one or more flavourings.

According to a second aspect of the present invention there is provided a method of manufacturing a Methotrexate composition suitable for oral administration, said method including the step of mixing a pharmaceutically acceptable salt of Methotrexate with an aqueous carrier agent until the Methotrexate salt is substantially or completely dissolved in the carrier agent to form an aqueous solution.

Preferably the method of manufacture takes place at room temperature (i.e. between 18-24° C.) and pressure.

The composition can be mixed together using any suitable mixing means.

Storage temperature of the resulting composition is also typically important in the stability of said composition.

Preferably the storage temperature of the resulting composition should be at approx. room temperature or within the temperature range of 18-25° C.

According to a further aspect of the present invention there is provided use of a Methotrexate composition in the manufacture of a medicament for the treatment in a patient as a folic acid antagonist, as an anti-neoplastic agent, an immunosuppressant, an anti-metabolite, neoplastic disease, malignant disease, psoriasis, Crohn's disease, rheumatoid arthritis, polyarthritic forms of active juvenile idiopathic arthritis, juvenile dermatomyositis, vasculitis, uvenlitis, systemic lupus erythematosus, localised scleroderma and/or sarcoidrosis, said composition containing a pharmaceutically acceptable salt of Methotrexate and an aqueous carrier agent in which the Methotrexate salt is substantially or completely soluble to form an aqueous solution Preferably the patient is a human patient.

Thus, the present invention provides a pharmaceutically effective, safe and simple to administer oral dosage form (i.e. oral solution) of Methotrexate that has an increased shelf life and which will benefit a patient group that has problems in swallowing.

BRIEF DESCRIPTION OF THE DRAWING

FIG. 1 is a graph showing results of analysis of the present invention.

DETAILED DESCRIPTION OF THE INVENTION

Detailed embodiments of the present invention will now be described.

Test 1

The Applicants initially undertook a study to calculate the pH at which a Methotrexate composition containing 10 mg/5 ml Methotrexate Disodium remained stable (i.e. showed little or no pH drift over time) and the buffering conditions that provided this stability. The samples in test 1 included Batch A which had the pH adjusted to pH 6 and included buffering agents; Batch B which had been adjusted to pH 6 but contained no buffering agents; and Batch C which had the pH adjusted to 7 and included buffering agents.

More particularly, Batch A included 250 ml of purified water, 5.72 g of Disodium Hydrogen Phosphate Dihydrate, 1.88 g of Citric Acid Monohydrate, 1.096 g* of Methotrexate Disodium and the formulation was made up to 500 ml in purified water. (*Methotrexate Disodium amount includes a QS calculation to account for the sodium salt and raw material water content to produce 10 mg/5 ml of Methotrexate base in the product). The pH was adjusted to pH 6.0 using 10% Citric Acid solution.

Batch B included 250 ml of purified water, 1.096 g* of Methotrexate Disodium and the formulation was made up to 500 ml in purified water. (*Methotrexate Disodium amount includes a QS calculation to account for the sodium salt and raw material water content to produce 10 mg/5 ml of Methotrexate base in the product). The pH was adjusted to pH 6.0 using 10% Citric Acid solution.

Batch C included 250 ml of purified water, 7.76 g of Disodium Hydrogen Phosphate Dihydrate, 0.68 g of Citric Acid Monohydrate, 1.096 g* of Methotrexate Disodium and the formulation was made up to 500 ml in purified water. (*Methotrexate Disodium amount includes a QS calculation to account for the sodium salt and raw material water content to produce 10 mg/5 ml of Methotrexate base in the product). The pH was adjusted to pH 7.0 using 10% Citric Acid solution.

Initially the temperature of the compositions was maintained at 25° C. and the pH was measured at the starting point (t=0), at week 2, week 4 and week 8. The results are shown in Table 1 below.

TABLE 1

| | | | Time-weeks | | | |
| --- | --- | --- | --- | --- | --- | --- |
| Batch | Variables | Condition | 0 | 2 | 4 | 8 |
| A | pH 6 Buffered | 25° C. | pH 5.98 | pH 6.09 | pH 6.15 | pH 6.18 |
| B | pH 6 Unbuffered | 25° C. | pH 6.36 | pH 6.51 | pH 6.59 | pH 7.22 |
| C | pH 7.0 Buffered | 25° C. | pH 6.93 | pH 7.02 | pH 7.10 | pH 7.17 |

NB: At the time of manufacture the pH of both the pH 6 buffered and pH 6 unbuffered formulations were adjusted to pH 6.00.

Firstly, the results show the instability of the pH of the composition when no buffering agents are used, based on the fact that at T=0 the unbuffered solution of Batch B had already increased to pH 6.36. This suggests that the pH of the Methotrexate solution drifted upwards in the short time between the end of manufacture of the composition and the testing of the samples.

The results from test 1 show that the buffered pH 6.0 and pH 7.0 formulations had minimal pH drift during the study.

The unbuffered pH 6.0 formulation showed a marked increase in pH during the study. This test demonstrated that the Methotrexate formulation required a buffer system to control pH drift and to stabilise the resulting composition.

The next test was undertaken to determine what effect a buffering system had on the levels of degradants present in a 10 mg/5 ml Methotrexate solution over time. The % of a known degradant (Impurity E) was measured using an HPLC assay. The same batch samples were made up as for test 1 and the conditions were maintained at 25° C. The % of degradation was measured at the start point (T=0), week 2, week 4 and week 8. The results are shown in Table 2 below.

TABLE 2

| Batch | Variables | Condition | Time-weeks | | | |
|---|---|---|---|---|---|---|
| | | | 0 | 2 | 4 | 8 |
| A | pH 6 Buffered | 25° C. | 0.00% | 0.00% | 0.00% | 0.13% |
| B | pH 6 Unbuffered | 25° C. | 0.02% | 0.10% | 0.16% | 0.68% |
| C | pH 7.0 Buffered | 25° C. | 0.00% | 0.12% | 0.19% | 1.80% |

The results show that even after 8 weeks, the levels of degradation in the Buffered pH 6 formulation remain low throughout the trial with only 0.13% for the 25° C. sample with a corresponding pH of 6.18.

The unbuffered pH 6 formulation showed a much higher level of degradation of 0.68% at a corresponding pH of 7.22.

This data also showed that without a buffer the Methotrexate 10 mg/5 ml formulation showed a tendency for the pH to drift upwards. However, if the pH drifts up to pH 7 or above, the level of the degradation increases rapidly which will limit the shelf-life of the product.

Therefore, it was concluded that it was preferable to use a buffer system in the formulation to obtain a level of stability sufficient for obtaining a prolonged shelf life of the product. In order to choose a suitable buffer system and to calculate the desired buffer strength, a buffer was chosen and comprised an 87 millimolar Citric Acid/Disodium Hydrogen phosphate buffer system. The initial formulation tried was as follows:

Example 1

| Ingredient | Weight/5 ml |
|---|---|
| Purified Water (A) | 3 ml |
| Methotrexate Disodium | QS to 10.97 mg |
| Sodium Methyl Hydroxybenzoate | QS to 4.80 mg |
| Sodium Ethyl Hydroxybenzoate | QS to 2.40 mg |
| Citric Acid Monohydrate | 25.0 mg |
| Disodium Hydrogen Phosphate Dihydrate | 57.2 mg |
| Sucralose | 2.5 mg |
| Raspberry Flavour 545742E | 10.0 mg |
| Purified Water (C) | To 5 ml |

QS—Quantum Satis (as much as is required to make up the required volume/weight).

However, on storage a yellow precipitate was seen which was identified as Methotrexate. Therefore further investigation work was carried out to try to identify the causative factors of the precipitate and resolve them.

Batches were prepared at various pHs in the range 5.6-6.0 and were prepared at ½, $1/10^{th}$ and $1/20^{th}$ the original buffer strength of example 1 (i.e. the citric acid monohydrate and disodium hydrogen phosphate dihydrate buffer system). The original buffer strength was taken from a citrate-phosphate buffer table (http://microscopy.berkeley.edu/Resorces/instruction/buffers.html).

Visual observations showed that both the pH1 and ionic strength of the buffer affected the rate of precipitation of the Methotrexate (i.e. the point in time at which precipitation is seen) and the amount of Methoprene precipitate produced.

The graph in FIG. 1 shows the results of the analysis of the filtered supernatant solution for the above Methotrexate formulation at ½ and $1/10^{th}$ original buffer strength at four different pH values; 5.6, 5.7, 5.8 and 5.9. The analysis is based on the fact that the lower the % of Methotrexate found in the supernatant (i.e. Assay % SA), the lower the amount of Methotrexate remains in solution i.e. fully dissolved. Samples of the supernatant above the precipitate were filtered through a Whatman No. 4 Piker Paper and was assayed using HPLC for the Methotrexate active component.

The results show that by increasing the pH of the formulation towards pH 6.0, this increases the amount of Methotrexate dissolved in the formulation.

The results also show that there is less Methotrexate dissolved when a ½ strength buffer system is used compared to the formulation using a $1/10^{th}$ strength buffer system. This in turn suggests that the Methotrexate composition of the present invention is more physically stable at a lower ionic buffer strength i.e. does not precipitate out of solution.

This analytical work is backed up by stability studies which are shown in Table 3 below. The stability studies were undertaken using the example 1 formulation but using either a citrate-phosphate buffer system at half the strength (i.e. 43 mmol) or $1/10^{th}$ of the strength (i.e. 8.7 mmol) compared to that of example 1. The formulations were adjusted to 5 different pH values; 5.6, 5.7, 5.8, 5.9 and 6.0. One set of formulations were stored at 5° C. and one set of formulations were stored at 25° C. for each buffer strength and each pH value for the duration of the study. The study took place over a 6 month time period.

TABLE 3

| | ½ Buffer strength (43 mmol) | | $1/10^{th}$ Buffer Strength (8.7 mmol) | |
|---|---|---|---|---|
| pH | 5° C. | 25° C. | 5° C. | 25° C. |
| 5.6. | PPT @ 1M | PPT @ 1M | PPT @ 1M | PPT @ 1M |
| 5.7 | PPT @ 1M | PPT @ 1M | PPT @ 1M | PPT @ 1M |
| 5.8 | PPT @ 1M | PPT @ 1M | PPT @ 1M | PPT @ 1M |
| 5.9 | PPT @ 1M | PPT @ 1M | PPT @ 1M | PPT @ 5M |
| 6.0 | CS @ 6M | CS @ 6M | CS @ 6M | CS @ 6M |

PPT—precipitate observed
CS—Clear Solution. No precipitate
1M represents 1 month time period
5M represents 5 month time period
6M represents 6 month time period The results show that visually there was a increase in the amount of Methotrexate in solution as the pH in the formulations increased from 5.6 to 5.9.

Table 4 shows the results of a similar test undertaken using a standard formulation with different ionic strengths of a citrate-phosphate buffer used and all the formulations adjusted to pH 6.0. One set of formulations were kept at 5° C. and one set of formulations were kept at 25° C. for the duration of the study.

Each formulation included 300 g Purified Water, 0.571 g of Sodium Methyl Hydroxybenzoate (equivalent of 0.96 g/L free acid), 0.281 g of Sodium Ethyl Hydroxybenzoate (equivalent to 0.48 g/L free acid), 0.25 g Sucralose, 1 g of Raspberry flavour, 1.293 g Methotrexate Disodium (QS to 2.194 g/L) and made up to 500 ml using Purified Water.

The Citrate-Phosphate control had 5.72 g Disodium Hydrogen Phosphate Dihydrate and 2.50 g of Citric Acid Monohydrate. The Citrate-Phosphate ½ strength buffer had 2.86 g Disodium Hydrogen Phosphate Dihydrate and 1.25 g of Citric Acid Monohydrate. The Citrate-Phosphate 1/10th strength buffer had 0.572 g Disodium Hydrogen Phosphate Dihydrate and 0250 g of Citric Acid Monohydrate. The Citrate-Phosphate 1/20$^{th}$ strength buffer had 0.286 g Disodium Hydrogen Phosphate Dihydrate and 0.125 g of Citric Acid Monohydrate.

TABLE 4

| Buffer | Strength | Test | 5° C. | 25° C. |
|---|---|---|---|---|
| Citrate-Phosphate (Control) | 87 mmol | Appearance Degradant (Impurity C) | PPT @ 2M NT | PPT @ 6M 0.97% @ 5M |
| Citrate-Phosphate (½ strength) | 43 mmol | Appearance Degradant (Impurity C) | PPT @ 3M NT | CS @ 6M 0.85% @ 5M |
| Citrate-Phosphate (1/10 strength) | 8.7 mmol | Appearance Degradant (Impurity C) | CS @ 6M NT | CS @ 6M 0.76% @ 5M |
| Citrate-Phosphate (1/20 strength) | 4.3 mmol | Appearance Degradant (Impurity C) | CS @ 6M NT | CS @ 6M 0.70% @ 5M |

NT—Not Tested
PPT—precipitate observed
CS—Clear Solution. No precipitate
2M represents 2 month time period
3M represents 3 month time period
6M represents 6 month time period The results in Table 4 show that the lower the ionic strength of the citrate phosphate buffer, the more stable the formulation is at pH 6.0. No precipitate is observed at a buffer strength of ≤8.7 mmol on storage at 5° C. There is also a decrease in the amount of degradation observed (impurity C) as the buffer strength is decreased.

Table 5 shows a similar test to that undertaken for Table 4 but a separate phosphate and citrate buffers were used.

The formulation of the phosphate buffer used in each sample included 180 g Purified Water, 0.3426 g of Sodium Methyl Hydroxybenzoate *1 (equivalent of 0.96 g/L free acid), 0.1686 g of Sodium Ethyl Hydroxybenzoate *1 (equivalent to 0.48 g/L free acid), 0.15 g Sucralose, 0.6 g of Raspberry flavour, 0.7758 g of Methorate Disodium (QS to 2.194 g/L) and made up to 300 ml using Purified Water.

In the 66 mmol phosphate buffer the formulation included 0.357 g of Disodium Hydrogen Phosphate Dihydrate and 2.82 g of Sodium Dihydrogen Phosphate Dihydrate. In the 33 mmol phosphate buffer the formulation included 0.1785 g of Disodium Hydrogen Phosphate Dihydrate and 1.41 g of Sodium Dihydrogen Phosphate Dihydrate. In the 6.6 mmol phosphate buffer the formulation included 0.0357 g of Disodium Hydrogen Phosphate Dihydrate and 0.282 g of Sodium Dihydrogen Phosphate Dihydrate. In the 3.3 mmol phosphate buffer the formulation included 0.0182 g of Disodium Hydrogen Phosphate Dihydrate and 0.141 g of Sodium Dihydrogen Phosphate Dihydrate.

The formulation of the citrate buffer used in each sample included 600 g Purified Water, 1.141 g of Sodium Methyl Hydroxybenzoate *1 (equivalent of 0.96 g/L free acid), 0.563 g of Sodium Ethyl Hydroxybenzoate *1 (equivalent to 0.48 g/L free acid), 0.50 g Sucralose, 2.0 g of Raspberry Flavour, 2.520 g of Methotrexate Disodium (QS to 2.194 g/L) and made up to 1000 ml using Purified Water.

In the 100 mmol citrate buffer the formulation included 25.7 g of Sodium Citrate and 2.65 g of Citric Acid Monohydrate. In the 4.3 mmol citrate buffer the formulation included 1.18 g of Sodium Citrate and 0.1155 g of Citric Acid Monohydrate.

TABLE 5

| Buffer | Strength | 5° C. | 25° C. |
|---|---|---|---|
| Phosphate | 66 mmol | PPT @ 2M | PPT @ 2M |
| Phosphate | 33 mmol | PPT @ 2M | CS @ 3M |
| Phosphate | 6.6 mmol | CS @ 3M | CS @ 3M |
| Phosphate | 3.3 mmol | CS @ 3M | CS @ 3M |
| Citrate | 87 mmol | PPT @ 1 week | PPT @ 1M |
| Citrate | 8.7 mmol | PPT @ 3M | CS @ 4M |

PPT—precipitate observed
CS—Clear Solution. No precipitate
2M represents 2 month time period
3M represents 3 month time period
6M represents 4 month time period The results in table 5 support the results in table 4 in that the lower the ionic strength of the buffer system used in the formulation at pH 6.0, the more stable the Methotrexate formulation was over time.

Example 2 below shows a further Methotrexate formulation according to an embodiment of the present invention.

Example 2

| Ingredient | Specification | Weight/5 ml | Weight/liter |
|---|---|---|---|
| Purified Water (A) | Ph.Eur | 3 ml | 600.00 g |
| Sodium Methyl Hydroxybenzoate | Ph.Eur | QS to 4.80 mg Free acid | QS to 0.96 g free acid |
| Sodium Ethyl Hydroxybenzoate | Ph.Eur | QS to 2.40 mg free acid | QS to 0.48 g free acid |
| Disodium Hydrogen Phoshate Dihydrate | Ph.Eur | 5.72 mg | 1.144 g |
| Citric Acid Monohydrate | Ph.Eur | 6.27 mg | 1.254 g |
| Raspberry Flavour 545742E | HSE | 10.0 mg | 2.00 g |
| Sucralose | USP | 2.5 mg | 500.00 mg |
| Purified water (B) | Ph.Eur | 0.375 ml | 75.00 g |
| Methotrexate Disodium (equivalent to 10 mg/5 ml Methotrexate base) | Ph.Eur | QS to 10.97 mg | QS to 2.194 g |
| Disodium Hydrogen Phosphate Dihydrate (as a 10% w/v solution) | HSE | QS to pH | QS to pH |
| Citric Acid Monohydrate (as a 10% w/v solution) | HSE | QS to pH | QS to pH |
| Purified Water (C) | Ph.Eur | To 5 ml | To 1000 ml (1010.0 g*) g |

*based on weight per ml of 1.010 g/ml)
Ph.Eur—European Pharmacopoeia
HSE—In House Standard
USP—United States Pharmacopoeia
QS—Quantum Satis (Methotrexate Disodium and the Sodium p-Hydroxybenzoate preservatives are hygroscopic, therefore will require QS calculations prior to dispensing and batch manufacture.)

An example method of manufacture is set out below for the formulation shown in example 2. This method is typically undertaken at room temperature and pressure and could be carried out using a propeller mixer or a high shear mixer for example.

Manufacturing Process
1. Add the aqueous carrier agent in the form of Purified Water (A) to the main manufacturing vessel.
2. Add the preservatives in the form of Sodium Methylhydroxybenzoate and Sodium Ethyl Hydroxybenzoate to the main vessel and mix until substantially dissolved using a suitable mixer.
3. Add the buffer agent Disodium Hydrogen Phosphate Dihydrate to the main vessel and mix until substantially dissolved using a suitable mixer.
4. Add the buffer agent Citric Acid Monohydrate to the main vessel and mix until substantially dissolved using a suitable mixer.
5. Add the flavouring agent in the form of Raspberry flavour to the main vessel and mix until substantially dispersed using a suitable mixer.
6. Add the sweetening agent in the form of Sucralose to the main vessel and mix until substantially dissolved using a suitable mixer.
7. Into a suitable dean separate stage vessel dispense aqueous carrier agent in the form of purified water (B).
8. Add the Methotrexate Disodium salt into the separate stage vessel and mix until substantially dissolved either by hand or using a suitable mixer.
9. Add the separate stage Methotrexate solution (from stage 8) into the main vessel and mix until substantially dispersed using a suitable mixer.
10. Check the pH. If it is outside the range of 6.25+/−0.15 adjust the pH until it is within this range by using either 10% w/v solution of Citric Acid Monohydrate to lower the pH or a 10% w/v solution of Disodium Hydrogen Phosphate Dihydrate to increase the pH.
11. Add Purified Water (C) to make to final weight and mix until substantially dispersed using a suitable mixer.
12. The finished product is filled into amber glass bottles.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is limited only by the scope of the attached claims, including the full range of equivalency to which each element thereof is entitled.

The invention claimed is:

1. A methotrexate composition for oral administration, said composition consisting of:
    methotrexate or a salt thereof;
    one or more buffer agents to adjust the pH of the composition, wherein the pH of the composition is 6 to 7;
    one or more preserving agents;
    one or more agents selected from flavouring compounds and sweetening agents; and
    purified water.

2. The methotrexate composition of claim 1, wherein the methotrexate or the salt thereof is the salt of methotrexate.

3. The methotrexate composition of claim 2, wherein the salt of methotrexate is methotrexate disodium.

4. The methotrexate composition of claim 2, wherein the salt of methotrexate is present in the composition at 2.5 mg/5 ml, 5 mg/5 ml, or 10 mg/5 ml.

5. The methotrexate composition of claim 2, wherein the salt of methotrexate is present in the composition in the range of 0.05 mg/1 ml to 20 mg/1 ml.

6. The methotrexate composition of claim 1, wherein the pH of the composition is in the range of pH 6.1-6.5.

7. The methotrexate composition of claim 1, wherein the pH of the composition is in the range of pH 6.6-6.9.

8. The methotrexate composition of claim 1, wherein the one or more buffer agents comprise citric acid, sodium citrate, sodium dihydrogen phosphate, disodium hydrogen phosphate, trometamol (tris), hydrochloric acid, ascorbic acid, sodium ascorbate, any of the abovementioned sodium salts replaced with potassium salts, or any combination thereof.

9. The methotrexate composition of claim 1, wherein the one or more buffer agents comprise citric acid-sodium citrate buffer, sodium dihydrogen phosphate-disodium hydrogen phosphate buffer, trometamol (tris)-hydrochloric acid buffer, trometamol (tris)-citric acid buffer, ascorbic acid-sodium ascorbate buffer, or any of the abovementioned sodium salts replaced with potassium salts.

10. The methotrexate composition of claim 1, wherein the one or more buffer agents comprise citric acid and sodium citrate.

11. The methotrexate composition of claim 1, wherein one or more buffer agents have a strength between 2 to 200 millimolar.

12. The methotrexate composition of claim 1, wherein the one or more buffer agents have a strength between 25 to 75 millimolar.

13. The methotrexate composition of claim 1, wherein the one or more buffer agents have a strength between 2 to 20 millimolar.

14. The methotrexate composition of claim 1, wherein the one or more preserving agents comprise sodium methyl hydroxybenzoate, sodium ethyl hydroxybenzoate, sodium propyl hydroxybenzoate, sodium benzoate, potassium sorbate, or a combination thereof.

15. The methotrexate composition of claim 1, wherein the one or more preserving agents comprise sodium methyl hydroxybenzoate and sodium propyl hydroxybenzoate.

16. The methotrexate composition of claim 1, comprising a sweetening agent.

17. The methotrexate composition of claim 16, wherein the sweetening agent comprises sucralose, acesulfame K, or any other water soluble sweetener.

18. The methotrexate composition of claim 1, comprising a flavouring compound.

19. The methotrexate composition of claim 1, wherein the composition is an aqueous solution and is free of methotrexate precipitation after stored at 5° C. for 3 months.

20. The methotrexate composition of claim 1, wherein the composition is an aqueous solution and is free of methotrexate precipitation after stored at 5° C. for 6 months.

* * * * *

UNITED STATES PATENT AND TRADEMARK OFFICE
CERTIFICATE OF CORRECTION

| | |
|---|---|
| PATENT NO. | : 11,969,503 B2 |
| APPLICATION NO. | : 17/470131 |
| DATED | : April 30, 2024 |
| INVENTOR(S) | : Carl Tierney et al. |

It is certified that error appears in the above-identified patent and that said Letters Patent is hereby corrected as shown below:

In the Specification

Column 7, Line 16: Correct "0250" to "0.250"

Signed and Sealed this
Ninth Day of July, 2024

*Katherine Kelly Vidal*

Katherine Kelly Vidal
*Director of the United States Patent and Trademark Office*